United States Patent [19]

Hayashi et al.

[11] 4,046,158
[45] Sept. 6, 1977

[54] APPARATUS FOR DILUTING GAS

[75] Inventors: Osamu Hayashi; Takahumi Inagaki, both of Kyoto; Yoshio Yanagita, Otu, all of Japan

[73] Assignee: Standard Technology, Inc., Kyoto, Japan

[21] Appl. No.: 718,317

[22] Filed: Aug. 27, 1976

[30] Foreign Application Priority Data

Jan. 30, 1976 Japan .................................. 51-9792

[51] Int. Cl.² ............................................ F16K 19/00
[52] U.S. Cl. ......................................... 137/88; 137/7;
137/597; 137/599; 137/604
[58] Field of Search ................. 137/7, 8, 88, 110, 597,
137/599, 604, 606

[56] References Cited
U.S. PATENT DOCUMENTS

| | | | |
|---|---|---|---|
| 3,417,779 | 12/1968 | Golay | 137/597 X |
| 3,464,434 | 9/1969 | Nielsen | 137/7 X |
| 3,886,971 | 6/1975 | Lundsgaard | 137/599 |

*Primary Examiner*—Robert G. Nilson
*Attorney, Agent, or Firm*—Wenderoth, Lind & Ponack

[57] ABSTRACT

An apparatus for diluting gas. The apparatus has a primary passage having at opposite ends an inlet for component gas and an inlet for a diluent gas, a secondary passage for collecting the mixture of the component gas and the diluent gas, and a plurality of gas pressure reducing tubes each having the same structure for reducing the pressure of gas flowing therethrough by the same amount and which are connected in parallel between the primary passage and the secondary passage. An exhaust outlet has a changeover device connected thereto and a plurality of exhaust passages each has one end connected with the change-over device, one exhaust passage having the other end connected to the primary passage between one inlet and the next adjacent pressure reducing tube, another exhaust passage having the other end connected to the primary passage between the other inlet and the next adjacent pressure reducing tube, and the remaining exhaust passages having their other ends connected to the primary passage between respective pairs of pressure reducing tubes. A pressure control device is connected to the secondary passage for making the pressure of the mixed gas in the secondary passage a definite pressure, and a pressure difference control device is connected between the primary and secondary passages for making the pressure difference between the primary passage and the secondary passage a definite constant value.

4 Claims, 4 Drawing Figures

APPARATUS FOR DILUTING GAS

The present invention relates to an apparatus for diluting gas which is used, for example, for preparation of a calibration curve in gas analysis.

Hitherto, in an analysis for a certain component in a gaseous system, the usual procedure has been to provide a plurality of specimen gas cylinders and prepare a calibration curve from the numerical values indicated by an analyser corresponding to concentrations of the said gaseous component in those specimen gas cylinders. However, from a practical standpoint, it is very difficult to get a set of specimen gases having the component gas in concentrations from 0 to 100% in equal intervals, since it is inevitable that there is a certain degree of error in the desired concentration in each specimen gas cylinder, and moreover, the degree of error has a tendency to increase with the decrease of the concentration.

On the other hand, there is known a method for the preparation of the calibration curve in which there is provided gases having a compound for which an analysis is to be made in various concentrations by changing the pressure difference between the ends of a capillary through which the compound is passed. However, errors sometimes occur in the operation of such a method, and to minimize such errors is very difficult if the method is carried out without sufficient skill.

As described above, it has hitherto been very difficult to get a set of gases having concentrations of the desired component from 0 to 100% in equal intervals, and, accordingly, it has also been difficult to provide a calibration curve of high accuracy.

The purpose of the present invention is to provide an apparatus which overcomes such drawbacks of the conventional techniques and which, moreover, has various advantages.

An example of the present invention will now be described with reference to the attached drawings, in which.

Figure 1:
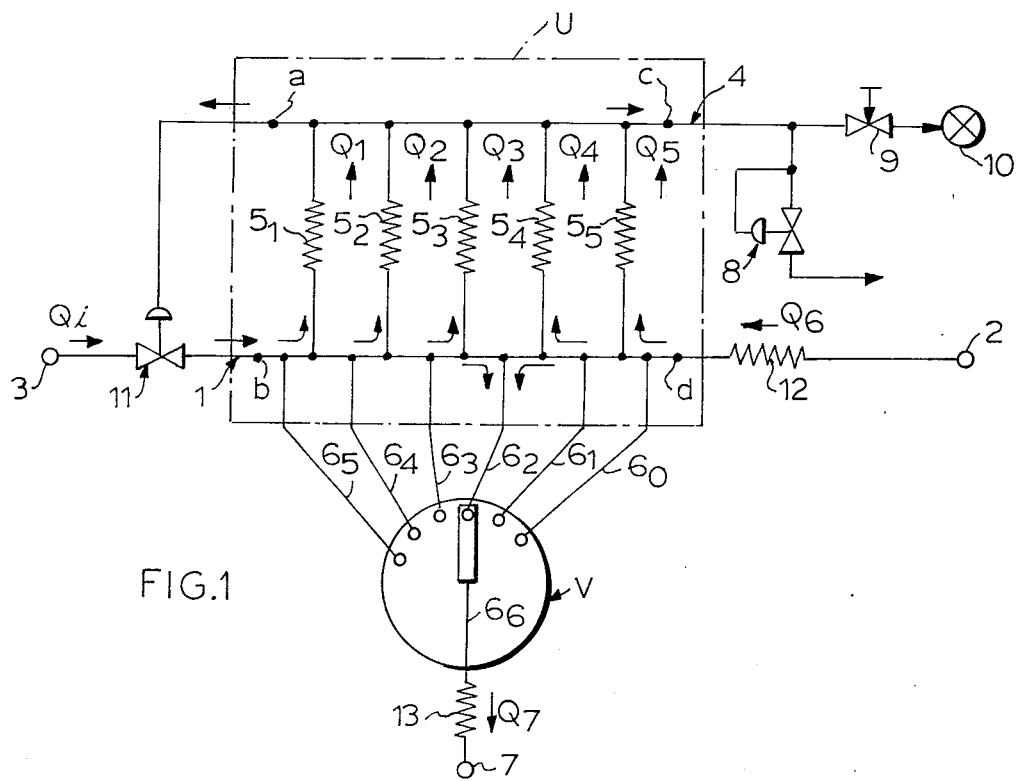
FIGS. 1 and 2 are schematic diagrams of a practical example of the apparatus according to the present invention.

As shown in FIG. 1, the apparatus has a primary passage 1 connecting an inlet 2 for a component gas (for example CO) and an inlet 3 for a diluent (for example such as $N_2$ gas). A secondary passage 4 is provided for collecting the mixture of the component gas and the diluent, and five capillaries $5_1$, $5_2$, $5_3$, $5_4$ and $5_5$ which have the same inner diameters and lengths are connected in parallel between the said primary passage 1 and the said secondary passage 4. Six exhaust passages $6_0$, $6_1$, $6_2$, $6_3$, $6_4$ and $6_5$ are connected between primary passage 1 and an exhaust outlet 7 through a change-over device V, for example, a cock or any other device having a structure able to selectively connect a common exhaust passage $6_6$ with any one of the six exhaust passages $6_0$, $6_1$, $6_2$, $6_3$, $6_4$ and $6_5$. The exhaust passages $6_0$–$6_5$ are, respectively, connected to the primary passage 1 between the component gas inlet 2 and the capillary $5_5$, and between the pairs of capillaries, and between the first capillary $5_1$ and the diluent inlet 3. A capillary 12 is connected between component gas inlet 2 and the primary passage 1, and a capillary 13 is connected to the outlet end of exhaust passage $6_6$.

Figure 2:
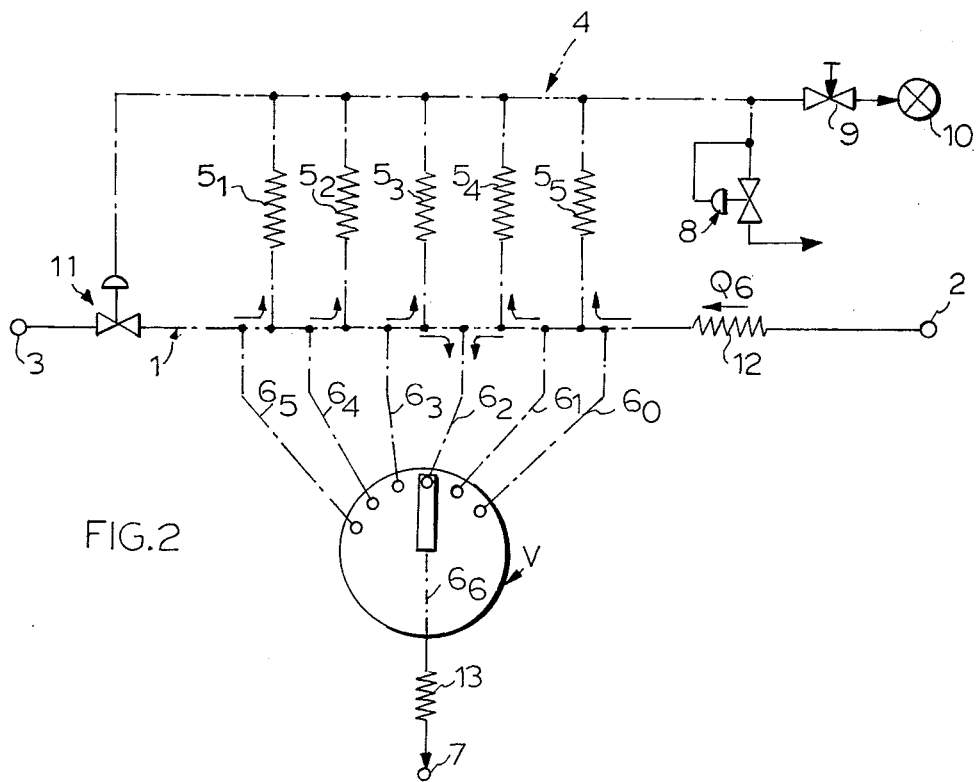

A back pressure regulator 8 is connected to the outlet end of the secondary passage 4 in order to maintain the pressure of the mixed gas in the secondary passage 4 at a constant level, and a throttle valve 9 is connected downstream of the pressure regulator 8 to adjust the pressure and the flow rate of the mixed gas which enters an analyser 10. The throttle valve 9 is unnecessary when the gas is discharged into the atmosphere. A pressure difference regulator 11 is connected between the diluent inlet 3 and the primary passage 1 and is connected to the upstream end of secondary passage 4 for maintaining the pressure difference between the primary passage 1 and the secondary passage 4 at a desired definite value, and as described above, since the pressure of the mixed gas in the secondary passage 4 is maintained at a constant level by the regulator 8, the pressure of gas in the primary passage is also constant, due to the action of the pressure difference regulator 11. In FIG. 2, the portions where the connections are shown by singly dotted lines are at one pressure of the mixed gas and the portions where the connections are shown by doubly dotted lines are at a second pressure.

The flow rates of gas passing through the capillaries $5_1$–$5_5$, 12 and 13 are denoted as $Q_1$, $Q_2$, $Q_3$, $Q_4$, $Q_5$, $Q_6$ and $Q_7$, respectively, wherein $Q_1$–$Q_5$ are all equal to each other since they are the flow rates through capillaries of the same size and at the same pressure condition, and $Q_6$ is a constant value.

In operation, if, for example, the change-over device V is operated to connect the exhaust passage $6_2$ with the exhaust passage $6_6$, as shown in FIGS. 1 and 2, the component gas and the diluent flow will be as shown by the arrows in FIGS. 1 and 2. Therefore, the concentration of the component gas flowing in the secondary passage 4 is given by the formula:

$$Q_4 + Q_5/Q_1+Q_2+Q_3+Q_4+Q_5 \text{ (component gas/Component gas + diluting gas)}$$

Thus, by selectively connecting any one of the six exhaust passages $6_0$–$6_5$ with the exhaust passage $6_6$ by the operation of the changeover device V, as described above, it becomes possible to obtain in secondary passage 4 a mixed gas in which the concentration of the component gas is 5/5, 4/5, 3/5, 2/5, 1/5 or 0/5, respectively.

Figure 3:
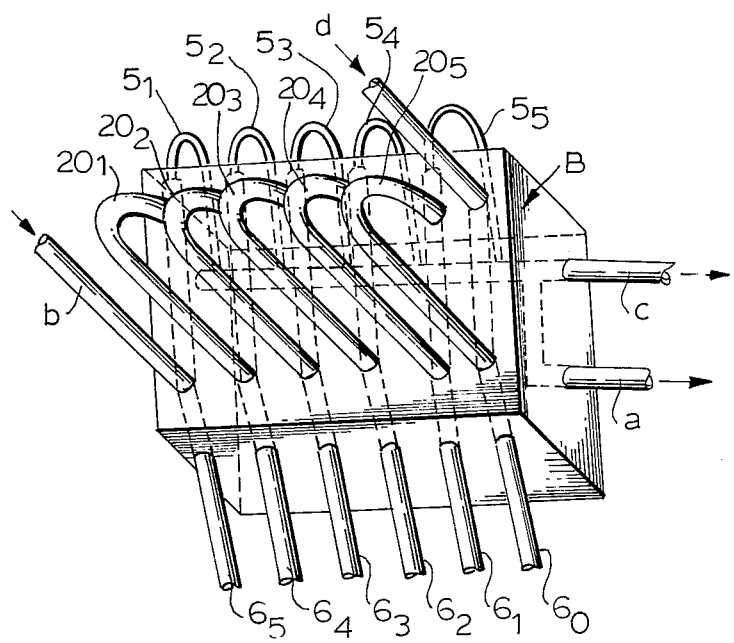
FIG. 3 is a perspective view of the apparatus of FIGS. 1 and 2.

FIG. 3 shows the structure of a practical embodiment of the portion U shown within chain lines in FIG. 1, wherein after preparing holes in a block B of stainless steel for passages of gas, as shown by the dotted lines in FIG. 3, capillaries $5_1$–$5_5$, exhaust passages $6_0$–$6_5$, and U-shaped pipes $20_1$, $20_2$, $20_3$, $20_4$ and $20_5$ of stainless steel for passages of gas are connected to the block B. The tubes shown at a, b, c and d in FIG. 3, respectively, correspond to the passages at the positions shown at a, b, c and d in FIG. 1.

Figure 4:
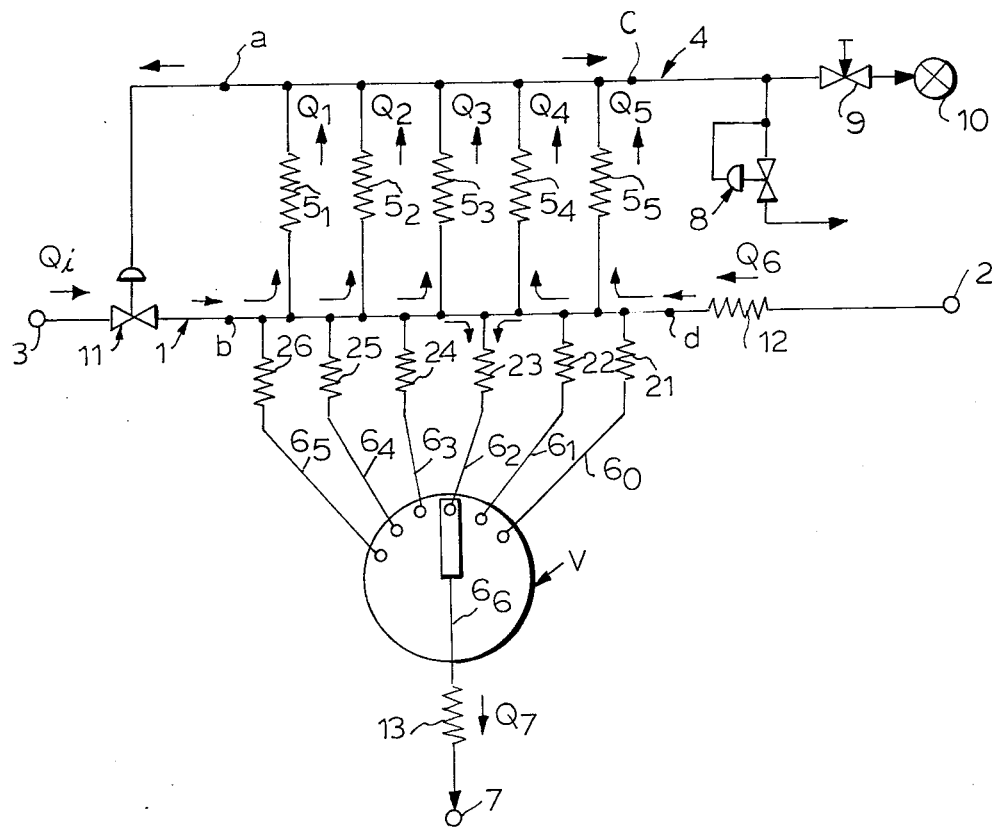
FIG. 4 is a schematic diagram of another example of the apparatus of the present invention.

Further, as shown in FIG. 4, it is possible to provide pressure reduction tubes 21, 22, 23, 24, 25 and 26 of the same inner diameter, such as capillary tubes, etc., in the exhaust passages $6_0$–$6_5$, respectively, which pressure reduction tubes are situated between the primary passage 1 and the change-over device V. By this arrangement, it becomes possible to reduce the consumption of diluent supplied into the primary passage, and, accordingly, this arrangement is desirable when the diluent is relatively expensive.

The reasons why the arrangement of FIG. 1 is advantageous can be understood from the following:

1. When only one capillary tube 13 is provided between the change-over device V and the exhaust outlet 7, as shown in FIG. 1, the pressure regulator 11 of FIG. 1 operates so as to maintain the pressure difference between the primary passage 1 and the secondary passage 4 at a constant level, holding the flow rate of the component gas $Q_6$ at a constant rate. $Q_6$ may be estimated as follows. If it is considered that the operating condition is such that the component gas is allowed to flow into all the capillaries $5_1$-$5_5$, that is, the exhaust passage $6_5$ is connected with the exhaust passage $6_6$, the rate of flow of the component gas $Q_6$ is the sum (which, of course, is a constant) of $Q_1 + Q_2 + Q_3 + Q_4 + Q_5$ and $\alpha 1$, wherein $\alpha_1$ is the low rate of flow of the component gas passing through the exhaust passage $6_5$, e.g. about 1/10 of Q1, and, as already mentioned, $Q_1 = Q_2 = Q_3 = Q_4 = Q_5$.

Making $Q_1 = q$, $Q_6$ can be given by the following relationship:

$$Q_6 = 5q + \alpha_1 \qquad (1)$$

wherein $\alpha_1 \approx (q/10)$.

If it is next considered that the diluent is allowed to flow into all the capillary tubes $5_1$-$5_5$, that is, the exhaust passage $6_0$ is connected with $6_6$, the total amount of the component gas flowing will be that which escapes through the exhaust passage $6_0$, and, moreover, a small amount of the diluent $\alpha_2$ will also escape through the passage $6_0$. Therefore, the flow rate of gas through the exhaust outlet $Q_7$ is given by the following relationship:

$$Q_7 = Q_6 + \alpha_2 \qquad (2)$$

wherein $\alpha_2 \approx (q/10)$ and $Q_6$ is given by (1).

If the flow rate of the diluent is denoted as $Q_i$, the total flow rate is given by the relationship (3), as follows:

$$Q_i + Q_6 = Q_1 + Q_2 + Q_3 + Q_4 + Q_5 + Q_7 \qquad (3).$$

From the relationships (1), (2) and (3), $$Q_i = 5q + \alpha_2 \qquad (4),$$

and, making $\alpha_2 \approx (q/10)$, then $Q_i \approx 5(1/10) q$.

From the above estimation, it is concluded that in the apparatus shown in FIG. 1, the amount of the diluent necessary for any mode of operation, regardless of whether the connection is made between any one of the exhausting passages $6_0$-$6_5$ and the passage $6_6$, is about 5 (1/10)$q$.

2. When capillary tubes 21-26 are provided in the exhaust passages $6_0$-$6_5$, respectively, as shown in FIG. 4, if exhaust passages $6_5$ and $6_6$ are connected, the flow rate $Q_6$ of the component gas is divided into two parts, that is, the one is $Q_1 + Q_2 + Q_3 + Q_4 + Q_5$ passing through the capillary tubes $5_1$-$5_5$, and the other is the flow rate through the capillary 26, given by $\alpha_1 = Q_6 - (Q_1 + Q_2 + Q_3 + Q_4 + Q_5)$, wherein $\alpha_1$ is a small value compared with $Q_6$. On the other hand, the amount of the diluent exhausted through the capillary 26 in the exhausting passage $6_5$ is small ($\alpha_2$) since it is only necessary to prevent the invasion of the component gas into the pressure regulator 11. That is, if the capillary 26 is given a small diameter which is sufficient to hold the necessary pressure difference between the ends of the capillaries $5_1$-$5_5$ by passing the small amount of gas $\alpha_1 + \alpha_2$ per unit time, the consumption of the diluent can be kept as small as $\alpha_2$.

If the exhaust passage $6_2$ is opened, connecting it with the exhaust passage $6_6$, the amount of the component gas which flows through the passage $6_2$ per unit time is given by $Q_6 - (Q_4 + Q_5) = 3q + \alpha_1$. Therefore, if the diameter of the capillary 23 is chosen to make it possible to maintain the desired pressure difference between the ends of the capillaries $5_1$-$5_5$ under a condition in which only a little more gas than the amount $Q_6 - (Q_4 + Q_5)$ is passed through the capillary 23, the amount of the diluent used per unit time is estimated to be only a little more than $Q_1 + Q_2 + Q_3$ or $(3q + \alpha_2)$.

The necessary amounts of the diluent for other cases where any one of passages other than those described above is opened for exhausting in the embodiment of FIG. 4 can be estimated in the same way as described above. The results can be summarized as follows:

1. when the exhaust passage $6_5$ is opened, the amount is $\alpha_2 (= q/10)$;
2. when the exhaust passage $6_4$ is opened, the amount is $q + \alpha_2$;
3. when the exhaust passage $6_3$ is opened, the amount is $2q + \alpha_2$;
4. when the exhaust passage $6_2$ is opened, the amount is $3q + \alpha_2$;
5. when the exhaust passage $6_1$ is opened, the amount is $4q + \alpha_2$; and
6. when the exhaust passage $6_0$ is opened, the amount is $5q + \alpha_2$.

Thus, for the embodiment of FIG. 4, the amount of the diluent is practically half that necessary for the embodiment of FIG. 1.

On the other hand, it can be pointed out that an advantage of the apparatus shown in FIG. 1 is that there is no change in the characteristics of pressure regulation due to changes in the flow rate of the constant pressure regulator 11, since the flow rate of the diluent through the regulator 11 reaches a steady state soon after start-up.

The apparatus for diluting gas according to the present invention as constructed as described above has the following characteristic features.

1. Since the plurality of constant pressure reduction tubes have the same structure, the effects of change of the pressure difference and change of temperature offset each other and have an almost negligible effect on the accuracy of the dilution of the gas. Furthermore, since the connections of the plurality of constant pressure reduction tubes having the same structure and the plurality of exhaust passages to the said primary passage alternate, it is possible to obtain a set of gases containing the component gas in concentrations from 0 to 100%, just as specified by an equi-difference partition, only by the operation of the change-over cock, and moreover, the operation itself is simple and does not produce errors, even if it is carried out by an unskilled operator.

2. There is no change-over device in the path of the mixed gas. This contributes to economy of space and to the rapid response, and there is no adsorption or desorption of the component gas by the change-over device. Accordingly, a superior accuracy in the concentration of the component gas can be achieved.

The present invention is, of course, not limited to the structures of the apparatus described as an example of the invention. It is possible to make many variations.

In FIG. 1, a constant pressure difference regulator can be arranged in the passage of the component gas, if the component gas has no tendency to adsorb or has only a small tendency of adsorption. That is, for example, the charge of the component gas from the inlet 3 and that of the diluent from inlet 2 is possible.

Furthermore, it may be possible to check the similarity of the capillaries, for example, by supplying a component gas to the said inlet 3 and a diluent to the inlet 2, then inversely, supplying the component gas from the inlet 2 and the diluent from the inlet 3.

In FIG. 4, a constant pressure difference regulator can also be provided in the passage of the component gas if the component gas has no tendency to adsorb or has only a small tendency of adsorption. That is, for example, the component gas can be supplied from the inlet 3 in FIG. 4 and the diluent from the inlet 2. In this case, the consumption of component gas, which is expensive, can be reduced.

What is claimed is:

1. An apparatus for diluting gas comprising a primary passage having at opposite ends an inlet for a component gas and an inlet for a diluent gas, a secondary passage for collecting the mixture of the component gas and the diluent gas, a plurality of gas pressure reducing tubes each having the same structure for reducing the pressure of gas flowing therethrough by the same amount and which are connected in parallel between said primary passage and said secondary passage, an exhaust outlet, a changeover device connected to said exhaust outlet, a plurality of exhaust passages each having one end connected with said change-over device, one exhaust passage having the other end connected to said primary passage between one inlet and the next adjacent pressure reducing tube, another exhaust passage having the other end connected to said primary passage between the other inlet and the next adjacent pressure reducing tube, and the remaining exhaust passages having their other ends connected to said primary passage between respective pairs of pressure reducing tubes, a pressure control device connected to said secondary passage for making the pressure of the mixed gas in the said secondary passage a definite pressure, and a pressure difference control device connected between said primary and secondary passages for making the pressure difference between the said primary passage and the secondary passage a definite constant value.

2. An apparatus as claimed in claim 1 in which said pressure reducing tubes are equal size capillaries.

3. An apparatus as claimed in claim 1 in which a capillary tube is provided between said changeover device and said exhaust outlet.

4. An apparatus as claimed in claim 1 in which a capillary tube is provided in each exhaust passage, said capillary tubes all being the same inner diameter.

* * * * *